US00PP30180P2

(12) United States Plant Patent
Kleinwee

(10) Patent No.: US PP30,180 P2
(45) Date of Patent: Feb. 5, 2019

(54) ***PETUNIA* PLANT NAMED 'PEHY0031'**

(50) Latin Name: *Petunia hybrida*
Varietal Denomination: PEHY0031

(71) Applicant: SYNGENTA PARTICIPATIONS AG, Basel (CH)

(72) Inventor: Theodorus Cornelis Maria Van Kleinwee, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/731,591

(22) Filed: Jul. 6, 2017

(51) Int. Cl.
*A01H 5/02* (2018.01)

(52) U.S. Cl.
USPC ..... Plt./356.22

(58) Field of Classification Search
USPC ..... Plt./356.22, 356.18

CPC . A01H 5/02; A01H 5/00; A01H 6/824; A01H 6/82

See application file for complete search history.

(56) References Cited

PUBLICATIONS

Issuu Syngenta FloriPro Services 2018 Annuals & Perennials, published on Jun. 11, 2017, retrieved on Jun. 5, 2018, retrieved from the Internet at https://issuu.corn/floriproservices/docs/a_p_2018_ex_150dpi, cover p. 72 and 228. (Year: 2017).*

Rośliny balkonowe 2018, magra.com.pl/wp-content.../Formularz-Etykiety_2018_DYS(2).xlsx -Excel, retrieved on Jun. 5, 2018, one page. (Year: 2018).*

* cited by examiner

*Primary Examiner* — June Hwu
(74) *Attorney, Agent, or Firm* — Dale Skalla

(57) ABSTRACT

A new *Petunia* plant named 'PEHY0031' particularly distinguished by small, purple flowers, a very good branching, flat habit and a very good field performance.

1 Drawing Sheet

Latin name of the genus and species of the plant claimed: *Petunia hybrida.*

Varietal denomination: 'PEHY0031'.

BACKGROUND OF THE NEW PLANT

The present invention comprises a new *Petunia*, botanically known as *Petunia hybrida*, and hereinafter referred to by the variety name 'PEHY0031'.

'PEHY0031' is a product of a planned breeding program. The new cultivar has small, purple flowers, a very good branching and flat habit and a very good field performance.

'PEHY0031' originated from a hybridization made in October 2010 in a controlled breeding environment in Enkhuizen, The Netherlands. The female parent was the unpatented proprietary plant designated 'M0601' with similar purple with vein flower color, but with bigger flower size, and a more upright to semi-trailing plant habit with less branching.

The male parent of 'PEHY0031' was variety 'PEHY0004' (U.S. Plant Pat. No. 23,432) a bicolor star pattern dark rose and light rose, with a comparable plant habit and more greyish-green colored leaves.

The resulting seeds were sown in January 2011. 'PEHY0031' was selected as one flowering plant within the progeny of the stated cross in May 2011 in a controlled environment in Enkhuizen, The Netherlands.

The first act of asexual reproduction of 'PEHY0031' was accomplished when stem tip vegetative cuttings were propagated from the initial selection in June 2011 in a controlled environment in Angers, France.

BRIEF SUMMARY OF INVENTION

Horticultural examination of plants grown from cuttings of the plant initiated in June 2011 and continuing thereafter, has demonstrated that the combination of characteristics as herein disclosed for 'PEHY0031' are firmly fixed and are retained through successive generations of asexual reproduction.

'PEHY0031' has not been observed under all possible environmental conditions. The phenotype may vary significantly with variations in environment such as temperature, light intensity, and day length.

A Plant Breeder's Right for this cultivar has not been applied for. 'PEHY0031' has not been made publicly available prior to the effective filing date of this application, notwithstanding any disclosure that may have been made less than one year prior to the effective filing date of this application by the inventor or another who obtained 'PEHY0031' directly from the inventor.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

The accompanying photographic drawing shows typical flower and foliage characteristics of 'PEHY0031' with colors being as true as possible with an illustration of this type.

Figure 1:
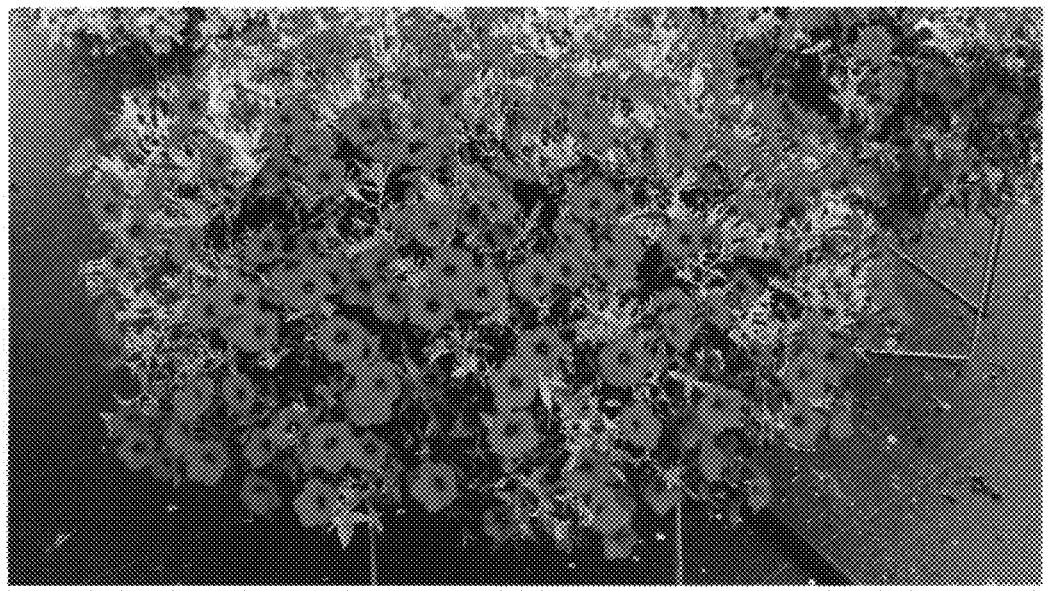
Figure 2:
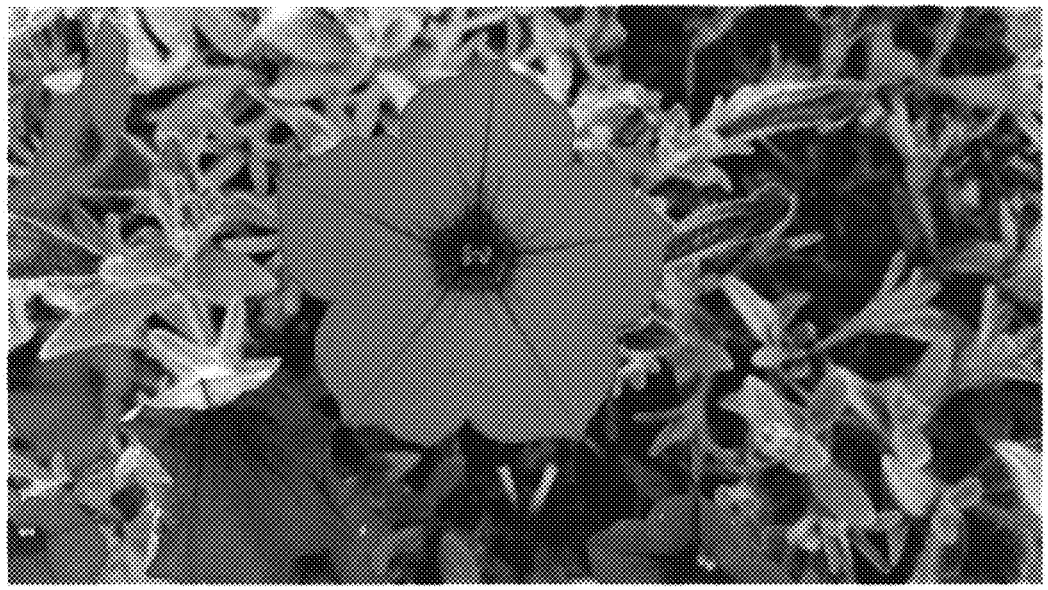

The photographic drawing shows in FIG. 1 a flowering plant of the new variety and in FIG. 2 a close-up of the flowers.

DETAILED BOTANICAL DESCRIPTION

The aforementioned photographs were taken in September 2016 from plants growing outside in Andijk, The Netherlands. These plants were approximately 22 weeks of age.

The plant descriptions and measurements were taken in October 2016 in Enkhuizen, The Netherlands on 23 week old plants that were growing in 25 cm pots.

Color references are made to The Royal Horticultural Society Colour Chart (R.H.S.) 2001.

TABLE 1

DIFFERENCES BETWEEN THE NEW VARIETY 'PEHY0031' AND A SIMILAR VARIETY

| | 'PEHY0031' | Whip Pur (U.S. Plant Pat. No. 15,480) |
|---|---|---|
| Plant habit: | Dense and flat growth | More open and upright plant habit |
| Vigor: | Strong | Very strong |
| Earliness: | Flowering 6 to 8 days earlier | Rather late flowering |

Plant:

*Form, growth and habit.*—Trailing, medium vigorous, very good branching plant.

*Plant height.*—13 cm.

*Plant height (inflorescence included).*—14 cm.

*Plant diameter (width).*—55 cm.

Roots:

*Number of days to initiate and produce roots.*—16 days at about 22 degrees C.

*Type.*—Fine, fibrous, free branching.

*Color.*—RHS N155B.

Foliage:

*Arrangement.*—Alternate, simple.

*Immature leaf, color upper surface.*—RHS 137C.

*Immature leaf, color lower surface.*—Closest to RHS 137D.

*Mature leaf, color upper surface.*—RHS 137B.

*Mature leaf, color lower surface.*—RHS 137D.

*Length.*—Up to 3.5 cm long.

*Width.*—Up to 1.8 cm wide.

*Shape.*—Ovate to elliptic.

*Base shape.*—Cuneate.

*Apex shape.*—Acute.

*Margin.*—Entire.

*Texture, upper surface.*—Moderate covered with short hairs.

*Lower surface.*—Moderate covered with short hairs, more densely covered with even shorter hairs on veins.

*Color of veins, upper surface.*—RHS 144A.

*Color of veins, lower surface.*—RHS 144A.

*Petiole color.*—RHS 144A.

*Length.*—0.1-0.3 cm.

*Diameter.*—0.2 cm.

*Petiole texture.*—Short glandular hairs.

Stem:

*Quantity of main branches per plant.*—8-9.

*Color of stem.*—RHS 144A.

*Length of stem.*—30-38 cm.

*Diameter.*—0.4 cm.

*Length of internodes.*—1-4 cm.

*Texture.*—Dense, mostly glandular hairs of various lengths.

*Color of pedicel.*—RHS 144A.

*Length of pedicel.*—1.0-1.5 cm.

*Diameter of pedicel.*—0.2 cm.

*Texture of pedicel.*—Densely covered with short hairs.

Inflorescence:

*Type.*—Flowers solitary in upper leaf axis.

*Floret type.*—Funnel-shaped; 5 lobed petals; fused at the base.

*Blooming habit.*—Continuous flowering throughout the summer months, excellent performance in warm and cool conditions.

*Quantity of inflorescences per plant.*—Approximately 100.

*Lastingness of individual blooms on the plant.*—About 7 days.

*Fragrance.*—A little scent.

Bud (just when opening):

*Color.*—RHS N92A.

*Length.*—2.7 cm.

*Width.*—0.6 cm.

*Shape.*—Oblong.

Immature inflorescence:

*Flower horizontal diameter.*—2.5 cm.

*Color petals, upper surface.*—Darker than RHS N74A.

*Color petals, lower surface.*—RHS 77A with veins RHS N77A.

Mature flower:

*Flower horizontal diameter.*—3.5 cm.

*Flower height (vertical).*—2.5 cm.

*Color upper surface.*—Darker than RHS N74A.

*Color lower surface.*—RHS 77A with veins RHS N77A, more greenish towards corolla tube, RHS 143B.

All petals:

*Apex shape.*—Cuspidate.

*Margin.*—Entire.

*Waviness of margin.*—Weak.

*Petal lobation.*—Medium.

*Petal texture, upper surface.*—Papillose, glabrous.

*Petal texture, lower surface.*—Papillose; glandular hair on veins and tube.

*Corolla tube color outside.*—RHS 79A.

*Corolla tube color inside.*—RHS 79B.

*Corolla tube length.*—2.0 cm.

*Corolla tube texture, outside.*—Pilose, glandular hairs.

*Corolla tube texture, inside.*—Glabrous.

Calyx:

*Color of sepal, upper surface.*—RHS 137B.

*Color of sepal, lower surface.*—RHS 137C.

*Length.*—0.9 cm.

*Width.*—0.2 cm.

*Shape.*—Ensiform.

*Apex shape.*—Acute to obtuse.

*Base.*—Fused.

*Margins.*—Entire.

*Texture, upper surface.*—Densely covered with short glandular hairs.

*Lower surface.*—Densily covered with short glandular hairs.

Reproductive organs:

*Pistil.*—1.

*Length.*—1.7 cm.

*Style color*.—RHS 137D, more anthocyanin towards stigma, RHS N79B.
*Style length*.—1.6 cm.
*Stigma color*.—RHS 137D.
*Stamens*.—
*Quantity per flower*.—5.
*Color of filaments*.—RHS N80C, lighter towards base.
*Length filaments*.—1.2 cm.
*Anther color*.—RHS N187C.
*Anther length*.—0.15 cm.
*Anther shape*.—Elliptical.
*Color of pollen*.—RHS N187D.
*Pollen amount*.—Moderate.
*Fertility/seed set*.—Has not been observed on this hybrid.
*Disease/pest resistance*.—Has not been observed on this hybrid.

What is claimed is:

1. A new and distinct variety of *Petunia* plant named 'PEHY0031' substantially as illustrated and described herein.

* * * * *